(12) United States Patent
Rodgers (10) Patent No.: US 6,838,263 B2
(45) Date of Patent: Jan. 4, 2005

(54) TARGETED FUSION PROTEINS AND METHODS FOR THE CHARACTERIZATION OF CELLULAR MEMBRANE DOMAINS

(75) Inventor: William Rodgers, Newalla, OK (US)

(73) Assignee: Oklahoma Medical Research Foundation, Oklahoma City, OK (US)

( * ) Notice: Subject to any disclaimer, the term of this patent is extended or adjusted under 35 U.S.C. 154(b) by 146 days.

(21) Appl. No.: 10/191,767

(22) Filed: Jul. 9, 2002

(65) Prior Publication Data

US 2003/0092132 A1 May 15, 2003

Related U.S. Application Data (60) Provisional application No. 60/304,030, filed on Jul. 9, 2001.

(51) Int. Cl.$^7$ ................................................. C12P 21/06
(52) U.S. Cl. ...................................................... 435/69.7
(58) Field of Search ......................... 435/69.1; 530/300, 530/350; 526/23.6

(56) References Cited

U.S. PATENT DOCUMENTS

| | | | |
|---|---|---|---|
| 6,342,379 B1 | 1/2002 | Tsien et al. ............... | 435/173.4 |
| 2002/0076729 A1 * | 6/2002 | Meyer et al. ................ | 435/7.2 |
| 2003/0066095 A1 | 4/2003 | Baubet et al. ................. | 800/3 |

OTHER PUBLICATIONS

Anders et al., "Effects of c–Src tyrosine kinase on ethanol sensitivity of recombinant NMDA receptors expressed in HEK 293 cells," *Alocoholism, Clinical and Experimental Research*, 23(2):357–362, 1999.

Bijlmakers and Marsh, "Hsp90 is essential for the synthesis and subsequent membrane association, but not the maintenance, of the Src–kinase p56(lck)," *Molecular Biology of the Cell*, 11(5):1585–1595, 2000.

Brown and London, "Functions of lipid rafts in biological membranes," *Annu. Rev. Cell Dev. Biol.*, 14:111–136, 1998.

Buckland et al., "Co–ordination of the expression of the protein tyrosine kinase p56(lck) with the pre–T cell receptor during thymocyte development," *European Journal of Immunology*, 30(1):8–18, 2000.

Chiu et al., "Trafficking of spontaneously endocytosed MHC proteins," *Proc. Natl. Acad. Sci. USA*, 96(24):13944–13949, 1999.

Janes et al., "Aggregation of lipid rafts accompanies signaling via the T cell antigen receptor," *J. of Cell Biology*, 147(2):447–461, 1999.

Kabouridis et al., "S–acylation of LCK protein tyrosine kinase is essential for its signaling function in T lymphocytes," *Embo. J.*, 16(16):4983–4998, 1997.

Karnitz et al., "Effects of p56$^{lck}$ deficiency on the growth and cytolytic effector functionof an interleukin–2–dependent cytotoxic T–cell line," *Mol. Cell Biol.*, 12:4521–4530, 1992.

Kwong and Lublin, "Amino–terminal palmitate of polybasic domain can provide required second signal to myristate for membrane binding of p56$^{lck}$," *Biochem. Biophys. Res. Commun.*, 207(2):868–876, 1995.

McCabe and Berthiaume, "Functional roles for fatty acylated amino–terminal domains in subcellular localization," *Molecular Biology of the Cell*, 10:3771–3786, 1999.

Nichols et al., "Rapid cycling of lipid raft markers between the cell surface and Golgi complex," *J. of Cell Biology*, 153(3):529–541, 2001.

Pyenta et al., "Cross–correlation analysis of inner–leaflet–anchored green fluorescent protein co–redistributed with Ige receptors and outer leaflet lipid raft components," *Biophysical Journal*, 80(5):2120–2132, 2001.

Resh, "Myristylation and palmitylation of Src family members: the fats of the matter," *Cell*, 76:411–413, 1994.

Rodgers and Rose, "Exclusion of CD45 inhibits activity of p56$^{lck}$ associated with glycolipid–enriched membrane domains," *J. Cell Biol.*, 135:1515–1523, 1996.

Rodgers et al., "Signals determining protein tyrosine kinase and glycosyl–phosphatidylinositol–anchored protein targeting to a glycolipid–enriched membrane fraction," *Mol. Cell Biol.*, 14:5384–5391, 1994.

Shenoy–Scaria et al., "Cysteine$^3$ of Src family tyrosine kinases determines palmitoylation and localization in caveolae," *J. Cell Biol.*, 126:353–363, 1994.

Shenoy–Scaria et al., "Palmitylation of an amino–terminal cysteine motif of protein tyrosine kinases p56$^{lck}$ and p59$^{fyn}$ mediates interaction with glycosyl–phosphatidylinositol–anchored proteins," *Mol. Cell Biol.*, 13:6385–6392, 1993.

Simons and Toomre, "Lipid rafts and signal transduction," *Nature Rev. Mol. Cell Biol.*, 1:31–39, 2000.

Straus and Weiss, "Genetic evidence for the involvement of the lck tyrosine kinase in signal transduction through the T cell antigen receptor," *Cell*, 70:585–593, 1992.

(List continued on next page.)

Primary Examiner—Karen Cochrane Carlson
Assistant Examiner—Sheridan K Snedden
(74) Attorney, Agent, or Firm—Fulbright & Jaworski, LLP (57) ABSTRACT

Cell membranes containing glycolipid-enriched membrane (GEM) and non-glycolipid-enriched membrane (non-GEM) domains are targeted using fusion proteins that are anchored in the cell membrane. Fusion proteins to target GEM (or non-GEM) domains are comprised of a selected fluorescent polypeptide, a membrane-targeting sequence of p56$^{Lck}$ (or pp60$^{c-Src}$ for non-GEM domains) and a linker inserted between the polypeptide and the membrane targeting sequence. Localization of fusion proteins in GEM and non-GEM domains is assessed using techniques including confocal microscopy, fluorescence-based techniques, and membrane fractionation. Using these techniques, compounds are screened for their effect on GEM and non-GEM domains of live cells. These fusion proteins therefore represent useful tools for studying subcellular trafficking and the function of discrete compartments in the plasma membrane.

10 Claims, 2 Drawing Sheets

OTHER PUBLICATIONS

Tansey et al., "GFRα–mediated localization of RET to lipid rafts is required for effective downstream signaling, differentiation, and neuronal survival," *Neuron*, 25(3):611–623, 2000.

Xavier et al., "Membrane compartmentation is required for efficient T cell activation," *Immunity*, 8:723–732, 1998.

Yurchak and Sefton, "Palmitoylation of either Cys–3 or Cys–5 is required for the biological activity of the Lck tyrosine protein kinase," *Mol. Cell Biol.*, 15:6914–6922, 1995.

Zacharias et al., "Partitioning of lipid–modified monomeric GFPs into membrane microdomains of live cells," *Science*, 296:913–916, 2002.

* cited by examiner

SEQUENCE LISTING

```
<160> NUMBER OF SEQ ID NOS: 4

<210> SEQ ID NO 1
<211> LENGTH: 42
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 1
atgggctgtg tctgcagctc aaaccctgaa aacaacaaca ac                          42

<210> SEQ ID NO 2
<211> LENGTH: 42
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 2
```

-continued gttgttgttg ttttcagggt ttgagctgca gacacagccc at          42

<210> SEQ ID NO 3
<211> LENGTH: 56
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 3
atggggagca gcaagagcaa gcccaaggac cccagccagc gccggaacaa caacaa          56

<210> SEQ ID NO 4
<211> LENGTH: 57
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 4
gttgttgttg ttccggcgct ggctggggtc cttgggcttg ctcttgctgc tccccat          57

TARGETED FUSION PROTEINS AND METHODS FOR THE CHARACTERIZATION OF CELLULAR MEMBRANE DOMAINS

This application is related to, and claims a benefit of priority from, provisional U.S. Provisional Ser. No. 60/304,030, filed Jul. 9, 2001, the entire contents of which are hereby expressly incorporated by reference for all purposes.

BACKGROUND OF THE INVENTION

I. Field of the Invention

This invention relates to the fields of cellular biology and membrane and protein biochemistry. In particular, the present invention provides fusion proteins encoding fluorescent proteins. The fusion proteins target glycolipid-enriched membrane (GEM) and non-glycolipid-enriched membrane (non-GEM) domains of cell membranes by virtue of membrane-anchoring signal from $p56^{lck}$ or $pp60^{c\text{-}src}$, respectively.

II. Background

The plasma membrane of mammalian cells contains domains representing distinct regions within the lipid bilayer with a composition that is different from the bulk composition of the plasma membrane. An important example of such domains are glycolipid-enriched membrane (GEM) domains (Simons and Toomre, 2000), also referred to as lipid rafts. Besides glycolipids, GEM domains are enriched with cholesterol and specific proteins, many of which function in cell signaling. The enrichment of signaling proteins in GEM domains has led to the notion that they represent a specialized signaling compartment within the plasma membrane. Importantly, recent studies corroborate this hypothesis. For example, in T cells, disruption of GEM domains also inhibits T cell activation (Xavier et al., 1998)

Despite the current interest in GEM domains, many of their properties remain elusive. This is due in part to the fact that many studies of GEM domains include detergent lysis of cells in order to separate the detergent-resistant GEM fraction from the non-GEM fraction of the plasma membrane. Obviously, such procedures are highly disruptive and, in addition to potentially altering the natural structure of such domains, the permit no follow-up experiments to explore further functional aspects. Thus, there remains a need to develop new and improved methods for examining GEM and non-GEM targeting in situ.

SUMMARY OF THE INVENTION

To avoid disruption of GEM domains, the inventors have developed methods for studying their properties in situ. Using these methods, GEM and non-GEM domains can be studied in intact cells using fluorescence imaging techniques such as confocal microscopy. The labeled targeting agents and methods described herein represent a advance in the characterization of GEM and non-GEM compartments of the plasma membrane in live cells.

Thus, in one aspect, the present invention provides a novel and useful method for studying the GEM and non-GEM domains of the plasma membrane of cells through the use of fusion proteins that are specifically targeted to these domains. In one embodiment, the invention provides for fusion proteins targeted to either GEM or non-GEM domains. In one embodiment, a fusion protein for targeting GEM domains is comprised of a peptide of 5 to about 15 consecutive amino acid residues comprising a membrane targeting sequence from $p56^{Lck}$, a fluorescent protein, and a linker inserted between, and covalently bound to, the membrane targeting sequence and the fluorescent protein. The membrane targeting sequence from $p56^{Lck}$ may comprise 5, 6, 7, 8, 9, 10, 11, 12, 13, 14, or 15 amino acid residues in length. Alternatively, the targeting sequence of the fusion protein may include the first 10 amino acid residues of $p56^{Lck}$. The fluorescent protein of the fusion protein may be green fluorescent protien, yellow fluorescent protein, or cyan fluorescent protein.

In another embodiment, a fusion protein for targeting non-GEM domains is comprised of a peptide of 10 to about 20 consecutive amino acid residues comprising a membrane targeting sequence from $pp60^{c\text{-}Src}$, a polypeptide encoding a fluorescent protein, and a linker inserted between, and covalently bound to, the membrane targeting sequence and the fluorescent protein. The membrane targeting sequence from $pp60^{c\text{-}Src}$ may comprise 10, 11, 12, 13, 14, 15, 16, 17, 18, 19 or 20 amino acid residues in length. The targeting sequence of the fusion protein may include the first 15 amino acid residues of $pp60^{c\text{-}Src}$. The fluorescent protein may be green fluorescent protein, yellow fluorescent protein, or cyan fluorescent protein.

For fusion proteins targeting to either GEM or non-GEM domains, the linker can be either a peptide or a non-peptide. In a preferred embodiment, the linker is a poly-glutamine peptide of about 4 amino acid residues in length.

Another embodiment of the current invention provides for polynucleotides that encode fusion proteins targeted to either the GEM or non-GEM domains of plasma membranes. A polynucleotide that encodes a fusion protein targeted to GEM domains is comprised of a peptide of 5 to about 15 consecutive amino acid residues comprising a membrane targeting sequence from $p56^{Lck}$, a polypeptide encoding a fluorescent protein, and a linker inserted between, and covalently bound to, said membrane targeting sequence and said fluorescent protein. In a particular embodiment, the targeting sequence and linker are encoded by the ATGGGCTGTGTCTGCAGCTCAAACCCT-GAAAACAACAACAAC. The linker can also be a poly-glutamine peptide of about 4 amino acid residues in length. The fluorescent protein may be green fluorescent protein, yellow fluorescent protein, or cyan fluorescent protein.

A polynucleotide that encodes a fusion protein targeted to non-GEM domains is comprised of a peptide of 10 to about 20 consecutive amino acid residues comprising a membrane targeting sequence from $pp60^{c\text{-}Src}$, a polypeptide encoding a fluorescent protein, and a linker inserted between, and covalently bound to, the membrane targeting sequence and the fluorescent protein. In a particular embodiment, the targeting sequence and linker are encoded by ATGGGGAG-CAGCAAGAGCAAGCCCAAGGACCCCAGC-CAGCGCCGGAACAACAACAA. The linker may also be a poly-glutamine peptide of about 4 amino acid residues in length. The fluorescent protein may be green fluorescent protein, yellow fluorescent protein, or cyan fluorescent protein.

Expression vectors comprising polynucleotides that encode fusion proteins targeted to GEM and non-GEM domains are also included in the present invention. In one embodiment, the expression vector is pWay20. In another embodiment, the promoter is a cytomegalovirus (CMV) promoter. The fluorescent protein may be green fluorescent protein, yellow fluorescent protein, or cyan fluorescent protein.

The present invention also provides for methods of targeting a protein to a GEM or non-GEM domain of a cell membrane. The method comprises providing a fusion protein and contacting the fusion protein with a cell. In this method, fusion proteins targeted to GEM domains are comprised of a peptide of 5 to about 15 residues comprising a membrane targeting sequence from p56$^{Lck}$, a fluorescent protein, and a linker inserted between, and covalently bound to, the membrane targeting sequence and the fluorescent protein. Alternatively, the fusion proteins are comprised of a peptide of 10 to about 20 residues comprising a membrane targeting sequence from pp60$^{c-Src}$, a fluorescent protein, and a linker inserted between, and covalently bound to the membrane targeting sequence and the fluorescent protein. The fluorescent protein of the fusion protein may be green fluorescent protein, yellow fluorescent protein, or cyan fluorescent protein The method of targeting a fusion protein to a GEM or non-GEM domain can further comprise an assessment of the location or localization of the fusion protein. This assessment can involve techniques including, but not limited to, immunoblotting. Fluorescence-based imaging techniques may be used to assess location or localization of the fusion protein, including use of cell imaging, flow cytometry, and fluorometry. In a preferred embodiment, confocal microscopy is used to assess the location of the fusion proteins. In addition, membrane fractionation may be used to assess location of fusion proteins within cell membranes.

The method of targeting a fusion protein to a GEM or non-GEM domain can also comprise providing a second fusion protein. In this method, the second fusion protein is comprised of a peptide of 5 to about 15 residues comprising a membrane targeting sequence from p56$^{Lck}$ or a peptide of 10 to about 20 consecutive amino acid residues comprising a membrane targeting sequence from pp60$^{c-Src}$, a fluorescent protein different from the fluorescent protein in the first fusion protein, and a linker inserted between, and covalently bound to, said membrane targeting sequence and said fluorescent protein; and the second fusion protein is contacted with a cell. The method may also comprising assessing the location or localization of the second fusion protein. The fluorescent protein of the second fusion protein may be green fluorescent protein, yellow fluorescent protein, or cyan fluorescent protein.

Finally, the present invention provides for a method of screening a compound for its effect on GEM and non-GEM domain targeting. The method includes providing a cell labeled with a fusion protein targeted to either GEM or non-GEM domains, admixing a candidate substance with the cell, and determining the effect of the candidate substance on GEM or non-GEM targeting. In this method, fusion proteins targeting to GEM domains are comprised of a peptide of 5 to about 15 residues comprising a membrane targeting sequence from p56$^{Lck}$, a fluorescent protein, and a linker inserted between, and covalently bound to, the membrane targeting sequence and the fluorscent protein. Alternatively, the fusion proteins are comprised of a peptide of 10 to about 20 residues comprising a membrane targeting sequence from pp60$^{c-Src}$, a fluorescent protein, and a linker inserted between, and covalently bound to, the membrane targeting sequence and the fluorescent protein.

The method of screening the effects of compounds may further comprise assessing the location or localization of the fusion protein. In a preferred embodiment, this assessment involves the use of confocal microscopy. Alternatively, immunoblotting and membrane fractionation may be used to assess the location of fusion proteins. Fluorescence-based techniques such as cell imaging, flow cytometry, and fluorometry may also be used to assess fusion protein localization. The fluorescent protein may be green fluorescent protein, yellow fluorescent protein, or cyan fluorescent protein.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIGS. 1A-1B: Targeting of GFP to GEM and non-GEM fractions in Jurkat T cells. (FIG. 1A) GFP was fused to the membrane-anchoring domain of either Lck (top) or c-Src (bottom). Each contains a poly-glutamine insert between the membrane-anchoring domain and GFP in order to add flexibility between the separate structural regions of the protein. (FIG. 1B) Measurement of GEM-association of L$_{10}$- and S$_{15}$-GFP by equilibrium centrifugation. Jurkat T cells expressing either protein were lysed with TX-100, and the GEM and TX-100 soluble (TXS) membrane fractions were separated by equilibrium centrifugation using a discontinuous sucrose gradient. Each protein was detected by immunoblotting using antibody that recognizes GFP. Fraction 1 represents the top of the gradient.

FIGS. 2A-2B: Measurement of targeting of GFP to membrane caps in stimulated T cells. In FIG. 2B, the relative enrichment of each GFP molecule at the bead contact site was measured and plotted for populations of stimulated Jurkat cells. Protein enrichment was measured using the ratio of average fluorescence intensity of the plasma membrane at the bead contact site divided by the average fluorescence intensity of the plasma membrane outside of the bead contact site.

DETAILED DESCRIPTION OF PREFERRED EMBODIMENTS

I. The Present Invention

As discussed above, glycolipid-enriched membrane (GEM) domains are enriched with cholesterol and specific proteins, many of which function in cell signaling. Despite the current interest in GEM domains, many of their properties remain elusive, due in large in part to the fact that most studies rely on detergent lysis of cells in order to separate the detergent-resistant GEM fraction from the non-GEM fraction of the plasma membrane.

The present invention overcomes such deficiencies in the art by providing compositions and methods that permit the study of GEM and non-GEM targeting in plasma membranes. In particular, the present invention involves the use of labeled fusion proteins that contain targeting signals for both GEM and non-GEM regions. These fusion proteins may be employed advantageously in gaining a better understanding of intracellular trafficking and in the screening of agents that alter the localization of peptides to either GEM or non-GEM regions of the membrane. In particular, the measurements will assess such functions as cell surface targeting, intracellular localization, and protein repartitioning, for example, as part of cellular activation.

II. Membrane-Targeted Fusion Proteins

A. $p56^{Lck}$ and $pp60^{cSrc}$

The presence of signaling proteins in GEM domains has led to the notion that they represent a specialized signaling compartment within the plasma membrane. One important signaling protein that associates with GEM domains is the Src protein tyrosine kinase $p56^{Lck}$ (Rodgers et al., 1994; Shenoy-Scaria et al., 1993). Association of $p56^{Lck}$ with GEM domains is noteworthy as it is essential for T cell development and stimulation (Karnitz et al., 1992); Straus et al., 1992). Furthermore, disruption of the GEM-targeting signal of $p56^{Lck}$ also inhibits T cell activation (Kabouridis et al., 1997).

Earlier studies have identified the GEM-targeting signal of many proteins that reside within GEM domains. In the case of $p56^{Lck}$, this consists of $Gly^2$, $Cys^3$, and $Cys^5$ (Rodgers et al., 1994; Shenoy-Scaria et al., 1994). Each of these residues is lipid-modified: $Gly^2$ is myristoylated and the cysteine residues are palmitoylated (Rodgers et al., 1994; Shenoy-Scaria et al., 1994; Yurchak et al., 1995). Replacement of either $Gly^2$ with alanine or $Cys^3$ and $Cys^5$ with serine disrupts both membrane and GEM association of $p56^{Lck}$ (Rodgers et al., 1994). Similarly, $pp60^{cSrc}$, whose membrane anchoring signal consists of myristoylation of $Gly^2$ followed by a string of basic amino acids but no palmitoylation (Resh, 1994) associates only with the non-GEM compartment of the plasma membrane (Kwong and Lublin, 1995).

A fusion or chimeric protein is a specialized kind of protein variant that is an insertional variant. This molecule generally has all or a substantial portion of the native molecule, linked at the N- or C-terminus or in even at other parts of the protein, to all or a portion of a second polypeptide. In the present invention, fusion proteins have been generated that comprise regions of the membrane-anchoring signal ($p56^{lck}$ or $pp60^{c-src}$). The regions involved with GEM and non-GEM targeting in $p56^{lck}$ or $pp60^{c-src}$ have been identified previously (Kwong and Lublin,1995; Shenoy-Scaria et al., 1994). However, it was unclear whether discrete portions of these molecules would be compatible in the context of a fluorescent protein fusion, and thus retain their targeting function.

Figure 1A:
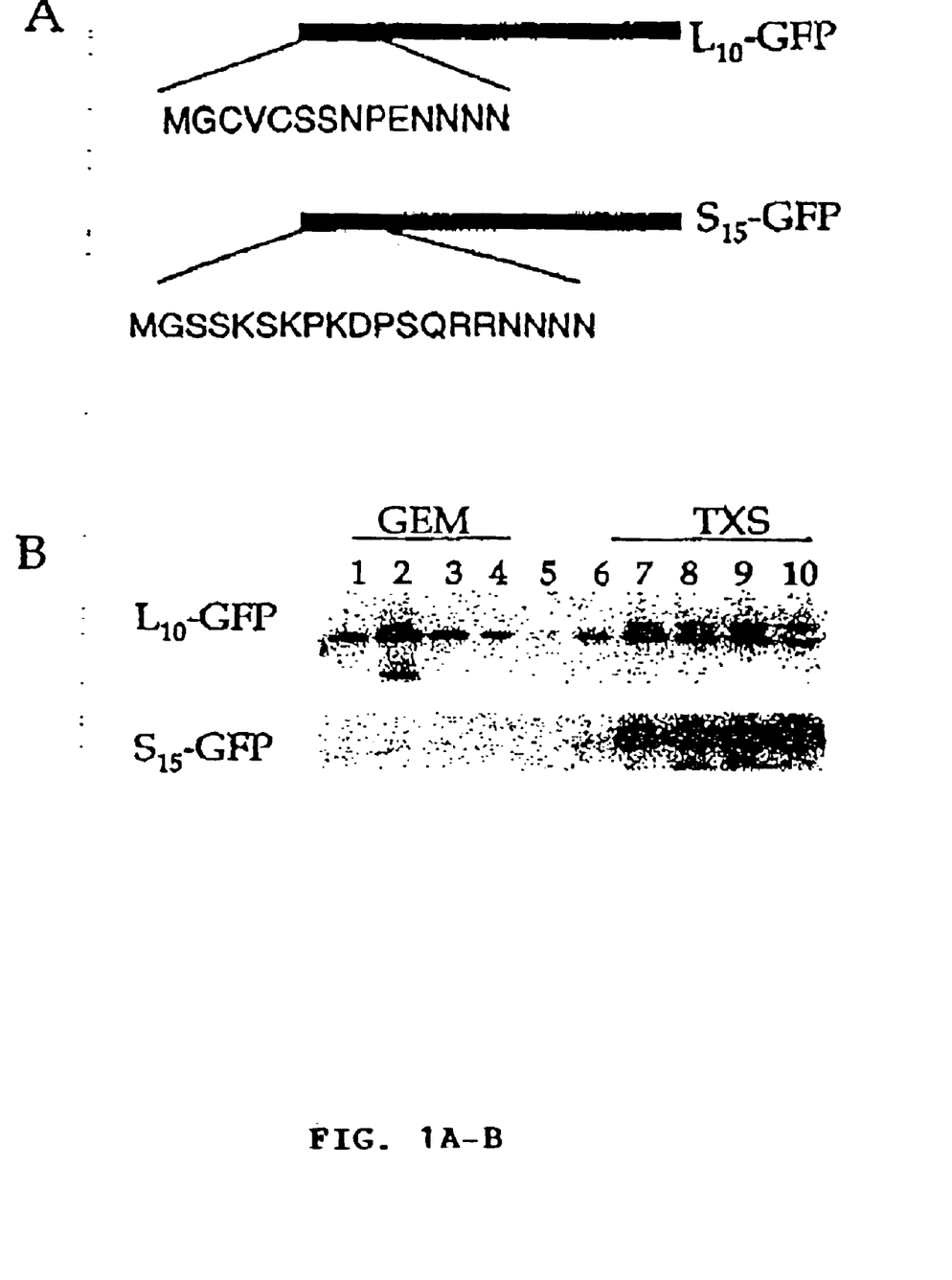

Thus, in accordance with the present invention, it has been demonstrated that regions as small as 10 residues of $p56^{Lck}$ and 15 residues of $pp60^{Src}$ retain their respective targeting functions when fused to fluorescent proteins. As shown in FIG. 1A, the $p56^{Lck}$ sequence of MGCVCSSNPE was used successfully to target GFP to GEM domains. The sequence MGSSKSKPKDPSQRR of $pp60^{Src}$ was used successfully to target GFP to non-GEM regions. It is believed that the carboxy-terminal five residues of each of these peptides may be removed while retaining their targeting function.

B. Fluorescent Proteins

The present invention contemplates fusion proteins comprising regions of proteins linked to fluorescent proteins such as green fluorescent proteins (GFP), (Chalfie et al. 1994; Prasher, 1995; WO 95/07463), cyan fluorescent proteins (CFP) (Heim and Tsien 1996), Accession #AB041904, and yellow fluorescent proteins (YFP) (Miyawaki et al., 1997). These fluorescent proteins may be used in combination to perform double-labeling studies by co-expressing the two colors together, as well as energy transfer measurements. Energy transfer is particularly useful for measuring distance between molecules in the 50–75 Angstrom range.

Several variants of GFP proteins have since been isolated, for example, the naturally-occurring blue fluorescent variant of GFP (Heim et al. 1994) and several other mutational variants, described in U.S. Pat. No. 6,172,188, incorporated herein by reference which allows the use of fluorescent probes having different excitation and emission spectra permits simultaneous monitoring of more than one process. GFP proteins provide non-invasive assays which allow detection of cellular events in intact, living cells. Other fluorescent or luminescent (e.g., proteins also could be employed).

C. Linkers/Coupling Agents

The fusion proteins of the present invention are comprised of a membrane-targeting signal (a region of $p56^{Lck}$ or $pp60^{cSrc}$) and a fluorescent protein joined via a linker, such as an amino acid sequence. An exemplary form of a peptide linker is a four-residue poly-glutamine insert. U.S. Pat. No. 5,856,456 provides peptide linkers for use in connecting polypeptide constituents to make fusion proteins. The linker is up to about 50 amino acids in length, contains at least one occurrence of a charged amino acid (preferably arginine or lysine) followed by a proline, and is characterized by greater stability and reduced aggregation. U.S. Pat. No. 5,880,270 discloses aminooxy-containing linkers useful in a variety of immunodiagnostic and separative techniques.

Additionally, any other linking/coupling agents known to those of skill in the art can be used according to the present invention, such as, for example, avidin-biotin linkages, amide linkages, ester linkages, thioester linkages, ether linkages, thioether linkages, phosphoester linkages, phosphoramide linkages, anhydride linkages, disulfide linkages, ionic and hydrophobic interactions, bispecific antibodies and antibody fragments, or combinations thereof.

Cross-linking reagents are used to form molecular bridges that tie together functional groups of two different molecules. To link two different compounds in a step-wise manner, hetero-bifunctional cross-linkers can be used that eliminate unwanted homopolymer formation. Table 1 lists such agents.

TABLE 1

HETERO-BIFUNCTIONAL CROSS-LINKERS

| linker | Reactive Toward | Advantages and Applications | Spacer Arm Length\after cross-linking |
|---|---|---|---|
| SMPT | Primary amines Sulfhydryls | Greater stability | 11.2 A |
| SPDP | Primary amines Sulfhydryls | Thiolation Cleavable cross-linking | 6.8 A |

TABLE 1-continued

HETERO-BIFUNCTIONAL CROSS-LINKERS

| linker | Reactive Toward | Advantages and Applications | Spacer Arm Length\after cross-linking |
|---|---|---|---|
| LC-SPDP | Primary amines Sulfhydryls | Extended spacer arm | 15.6 A |
| Sulfo-LC-SPDP | Primary amines Sulfhydryls | Extended spacer arm Water-soluble | 15.6 A |
| SMCC | Primary amines Sulfhydryls | Stable maleimide reactive group Enzyme-antibody conjugation Hapten-carrier protein conjugation | 11.6 A |
| Sulfo-SMCC | Primary amines Sulfhydryls | Stable maleimide reactive group Water-soluble Enzyme-antibody conjugation | 11.6 A |
| MBS | Primary amines Sulfhydryls | Enzyme-antibody conjugation Hapten-carrier protein conjugation | 9.9 A |
| Sulfo-MBS | Primary amines Sulfhydryls | Water-soluble | 9.9 A |
| SIAB | Primary amines Sulfhydryls | Enzyme-antibody conjugation | 10.6 A |
| Sulfo-SIAB | Primary amines Sulfhydryls | Water-soluble | 10.6 A |
| SMPB | Primary amines Sulfhydryls | Extended spacer arm Enzyme-antibody conjugation | 14.5 A |
| Sulfo-SMPB | Primary amines Sulfhydryls | Extended spacer arm Water-soluble | 14.5 A |
| EDC/Sulfo-NHS | Primary amines Carboxyl groups | Hapten-Carrier conjugation | 0 |
| ABH | Carbohydrates Nonselective | Reacts with sugar groups | 11.9 A |

An exemplary hetero-bifunctional cross-linker contains two reactive groups: one reacting with primary amine group (e.g., N-hydroxy succinimide) and the other reacting with a thiol group (e.g., pyridyl disulfide, maleimides, halogens, etc.). Through the primary amine reactive group, the cross-linker may react with the lysine residue(s) of one protein (e.g., the selected antibody or fragment) and through the thiol reactive group, the cross-linker, already tied up to the first protein, reacts with the cysteine residue (free sulfhydryl group) of the other protein (e.g., the selective agent).

Another cross-linking reagent is SMPT, which is a bifunctional cross-linker containing a disulfide bond that is "sterically hindered" by an adjacent benzene ring and methyl groups. It is believed that steric hindrance of the disulfide bond serves a function of protecting the bond from attack by thiolate anions such as glutathione which can be present in tissues and blood, and thereby help in preventing decoupling of the conjugate prior to the delivery of the attached agent to the target site.

The SMPT cross-linking reagent, as with many other known cross-linking reagents, lends the ability to cross-link functional groups such as the SH of cysteine or primary amines (e.g., the epsilon amino group of lysine). Another possible type of cross-linker includes the hetero-bifunctional photoreactive phenylazides containing a cleavable disulfide bond such as sulfosuccinimidyl-2-(p-azido salicylamido) ethyl-1,3'-dithiopropionate. The N-hydroxy-succinimidyl group reacts with primary amino groups and the phenylazide (upon photolysis) reacts non-selectively with any amino acid residue.

In addition to hindered cross-linkers, non-hindered linkers also can be employed in accordance herewith. Other useful cross-linkers, not considered to contain or generate a protected disulfide, include SATA, SPDP and 2-iminothiolane (Wawrzynczak & Thorpe, 1987). The use of such cross-linkers is well understood in the art.

U.S. Pat. No. 4,680,338, describes bifunctional linkers useful for producing conjugates of ligands with amine-containing polymers and/or proteins, especially for forming antibody conjugates with chelators, drugs, enzymes, detectable labels and the like. U.S. Pat. Nos. 5,141,648 and 5,563,250 disclose cleavable conjugates containing a labile bond that is cleavable under a variety of mild conditions. This linker is particularly useful in that the agent of interest may be bonded directly to the linker, with cleavage resulting in release of the active agent.

III. Nucleic Acid Compositions

A. General

Certain embodiments of the present invention concern polynucleotides that encode fusion proteins. The term "nucleic acid" is well known in the art. A "nucleic acid" as used herein will generally refer to a molecule (i.e., a strand) of DNA, RNA or a derivative or analog thereof, comprising a nucleobase. A nucleobase includes, for example, a naturally occurring purine or pyrimidine base found in DNA (e.g., an adenine "A," a guanine "G," a thymine "T" or a cytosine "C") or RNA (e.g., an A, a G, an uracil "U" or a C). The term "nucleic acid" encompass the terms "oligonucleotide" and "polynucleotide," each as a subgenus of the term "nucleic acid." The term "oligonucleotide" refers to a molecule of between about 3 and about 100 nucleobases in length. The term "polynucleotide" refers to at least one molecule of greater than about 100 nucleobases in length.

These definitions generally refer to a single-stranded molecule, but in specific embodiments will also encompass an additional strand that is partially, substantially or fully complementary to the single-stranded molecule. Thus, a nucleic acid may encompass a double-stranded molecule or a triple-stranded molecule that comprises one or more complementary strand(s) or "complement(s)" of a particular sequence comprising a molecule. As used herein, a single stranded nucleic acid may be denoted by the prefix "ss," a double stranded nucleic acid by the prefix "ds," and a triple stranded nucleic acid by the prefix "ts."

B. Preparation of Nucleic Acids

A nucleic acid may be made by any technique known to one of ordinary skill in the art, such as for example, chemical synthesis, enzymatic production or biological production. Non-limiting examples of a synthetic nucleic acid (e.g., a synthetic oligonucleotide), include a nucleic acid made by in vitro chemically synthesis using phosphotriester, phosphite or phosphoramidite chemistry and solid phase techniques such as described in EP 266 032, incorporated herein by reference, or via deoxynucleoside H-phosphonate intermediates as described by Froehler et al., 1986, incorporated herein by reference. In the methods of the present invention, one or more oligonucleotide may be used. Various different mechanisms of oligonucleotide synthesis have been disclosed in for example, U.S. Pat. Nos. 4,659,774, 4,816,571, 5,141,813, 5,264,566, 4,959,463, 5,428,148, 5,554,744, 5,574,146, 5,602,244, each of which is incorporated herein by reference.

A non-limiting example of an enzymatically produced nucleic acid includes one produced by enzymes in amplification reactions such as PCR™ (see for example, U.S. Pat. No. 4,683,202 and U.S. Pat. No. 4,682,195, each incorporated herein by reference), or the synthesis of an oligonucleotide described in U.S. Pat. No. 5,645,897, incorporated herein by reference. A non-limiting example of a biologically produced nucleic acid includes a recombinant nucleic acid produced (i.e., replicated) in a living cell, such as a recombinant DNA vector replicated in bacteria (see for example, Sambrook et al. 1989, incorporated herein by reference).

C. Purification of Nucleic Acids

A nucleic acid may be purified on polyacrylamide gels, cesium chloride centrifugation gradients, or by any other means known to one of ordinary skill in the art (see for example, Sambrook et al., 1989, incorporated herein by reference).

In certain aspect, the present invention concerns a nucleic acid that is an isolated nucleic acid. As used herein, the term "isolated nucleic acid" refers to a nucleic acid molecule (e.g., an RNA or DNA molecule) that has been isolated free of, or is otherwise free of, the bulk of the total genomic and transcribed nucleic acids of one or more cells. In certain embodiments, "isolated nucleic acid" refers to a nucleic acid that has been isolated free of, or is otherwise free of, bulk of cellular components or in vitro reaction components such as for example, macromolecules such as lipids or proteins, small biological molecules, and the like.

D. Regulatory Components and Expression Constructs

The nucleic acid(s) of the present invention, regardless of the length of the sequence itself, may be combined with other nucleic acid sequences, including but not limited to, promoters, enhancers, polyadenylation signals, restriction enzyme sites, multiple cloning sites, coding segments, and the like, to create one or more nucleic acid construct(s). As used herein, a "nucleic acid construct" is a nucleic acid engineered or altered by the hand of man, and generally comprises one or more nucleic acid sequences organized by the hand of man.

In particular embodiments, the invention concerns one or more recombinant vector(s) comprising nucleic acid sequences that encodes a fusion protein comprised of a membrane targeting sequence of p56$^{Lck}$ or pp60$^{cSrc}$, a polypeptide encoding fluorescent proteins, and a linker inserted between, and covalently bound to, the membrane targeting sequence of fluorescent proteins. In particular aspects, the recombinant vectors are DNA vectors.

The term "functionally equivalent codon" is used herein to refer to codons that encode the same amino acid, such as the six codons for arginine and serine, and also refers to codons that encode biologically equivalent amino acids. Codons are shown in Table 2 in preference of human use from left to right. Thus, the most preferred codon for alanine is thus "GCC", and the least is "GCG" (see Table 2, below).

TABLE 2

Preferred Human DNA Codons

| Amino Acids | | Codons |
|---|---|---|
| Alanine | Ala A | GCC GCT GCA GCG |
| Cysteine | Cys C | TGC TGT |
| Aspartic acid | Asp D | GAC GAT |
| Glutamic acid | Glu E | GAG GAA |
| Phenylalanine | Phe F | TTC TTT |
| Glycine | Gly G | GGC GGG GGA GGT |
| Histidine | His H | CAC CAT |
| Isoleucine | Ile I | ATC ATT ATA |
| Lysine | Lys K | AAG AAA |
| Leucine | Leu L | CTG CTC TTG CTT CTA TTA |
| Methionine | Met M | ATG |
| Asparagine | Asn N | AAC AAT |
| Proline | Pro P | CCC CCT CCA CCG |
| Glutamine | Gln Q | CAG CAA |
| Arginine | Arg R | CGC AGG CGG AGA CGA CGT |
| Serine | Ser S | AGC TCC TCT AGT TCA TCG |
| Threonine | Thr T | ACC ACA ACT ACG |
| Valine | Val V | GTG GTC GTT GTA |
| Tryptophan | Trp W | TGG |
| Tyrosine | Tyr Y | TAC TAT |

It will also be understood that amino acid sequences or nucleic acid sequences may include additional residues, such as additional N- or C-terminal amino acids or 5' or 3' sequences, or various combinations thereof, and yet still be essentially as set forth in one of the sequences disclosed herein, so long as the sequence meets the criteria set forth above, including the maintenance of biological protein, polypeptide or peptide activity where expression of a proteinaceous composition is concerned. The addition of terminal sequences particularly applies to nucleic acid sequences that may, for example, include various non-coding sequences flanking either of the 5' and/or 3' portions of the coding region or may include various internal sequences, i.e., introns, which are known to occur within genes.

It will also be understood that this invention is not limited to the particular nucleic acid or amino acid sequences of the fusion proteins. Recombinant vectors and isolated nucleic acid segments may therefore variously include these coding regions themselves, coding regions bearing selected alterations or modifications in the basic coding region, and they may encode larger polypeptides or peptides that nevertheless include such coding regions or may encode biologically functional equivalent proteins, polypeptide or peptides that have variant amino acids sequences.

The nucleic acids of the present invention encompass biologically functional equivalent fusion proteins or polypeptides. Such sequences may arise as a consequence of codon redundancy or functional equivalency that are known to occur naturally within nucleic acid sequences or the proteins, polypeptides or peptides thus encoded. Alternatively, functionally equivalent proteins, polypeptides or peptides may be created via the application of recombinant DNA technology, in which changes in the protein, polypeptide or peptide structure may be engineered, based on considerations of the properties of the amino acids being exchanged. Changes designed by man may be introduced, for example, through the application of site-directed mutagenesis techniques as discussed herein below, e.g., to introduce improvements or alterations to the antigenicity of the protein, polypeptide or peptide, or to test mutants in order to examine the activity of the fusion protein at the molecular level.

IV. Nucleic Acid-Based Expression Systems

A. Vectors

The term "vector" is used to refer to a carrier nucleic acid molecule into which a nucleic acid sequence can be inserted for introduction into a cell where it can be replicated. A nucleic acid sequence can be "exogenous," which means that it is foreign to the cell into which the vector is being introduced or that the sequence is homologous to a sequence in the cell but in a position within the host cell nucleic acid in which the sequence is ordinarily not found. Vectors include plasmids, cosmids, viruses (bacteriophage, animal viruses, and plant viruses), and artificial chromosomes (e.g., YACs). One of skill in the art would be well equipped to construct a vector through standard recombinant techniques (see, for example, Maniatis et al., 1988 and Ausubel et al., 1994, both incorporated herein by reference). In the present invention, a preferred expression vector is pWay20 (Lo and Hughes, 1998).

The term "expression vector" refers to any type of genetic construct comprising a nucleic acid coding for a RNA capable of being transcribed. In some cases, RNA molecules are then translated into a protein, polypeptide, or peptide. In other cases, these sequences are not translated, for example, in the production of antisense molecules or ribozymes. Expression vectors can contain a variety of "control sequences," which refer to nucleic acid sequences necessary for the transcription and possibly translation of an operably linked coding sequence in a particular host cell. In addition to control sequences that govern transcription and translation, vectors and expression vectors may contain nucleic acid sequences that serve other functions as well and are described infra.

1. Promoters and Enhancers

A "promoter" is a control sequence that is a region of a nucleic acid sequence at which initiation and rate of transcription are controlled. It may contain genetic elements at which regulatory proteins and molecules may bind, such as RNA polymerase and other transcription factors, to initiate the specific transcription a nucleic acid sequence. The phrases "operatively positioned," "operatively linked," "under control," and "under transcriptional control" mean that a promoter is in a correct functional location and/or orientation in relation to a nucleic acid sequence to control transcriptional initiation and/or expression of that sequence.

A promoter generally comprises a sequence that functions to position the start site for RNA synthesis. The best known example of this is the TATA box, but in some promoters lacking a TATA box, such as, for example, the promoter for the mammalian terminal deoxynucleotidyl transferase gene and the promoter for the SV40 late genes, a discrete element overlying the start site itself helps to fix the place of initiation. Additional promoter elements regulate the frequency of transcriptional initiation. Typically, these are located in the region 30–110 bp upstream of the start site, although a number of promoters have been shown to contain functional elements downstream of the start site as well. To bring a coding sequence "under the control of" a promoter, one positions the 5 end of the transcription initiation site of the transcriptional reading frame "downstream" of (i.e., 3 of) the chosen promoter. The "upstream" promoter stimulates transcription of the DNA and promotes expression of the encoded RNA.

The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either cooperatively or independently to activate transcription. A promoter may or may not be used in conjunction with an "enhancer," which refers to a cis-acting regulatory sequence involved in the transcriptional activation of a nucleic acid sequence.

A promoter may be one naturally associated with a nucleic acid sequence, as may be obtained by isolating the 5 non-coding sequences located upstream of the coding segment and/or exon. Such a promoter can be referred to as "endogenous." Similarly, an enhancer may be one naturally associated with a nucleic acid sequence, located either downstream or upstream of that sequence. Alternatively, certain advantages will be gained by positioning the coding nucleic acid segment under the control of a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural environment. Such promoters or enhancers may include promoters or enhancers of other genes, and promoters or enhancers isolated from any other virus, or prokaryotic or eukaryotic cell, and promoters or enhancers not "naturally occurring," i.e., containing different elements of different transcriptional regulatory regions, and/or mutations that alter expression. For example, in a preferred embodiment of the present invention, the promoter is a cytomegalovirus (CMV) promoter. Promoters that are most commonly used in recombinant DNA construction include the -lactamase (penicillinase), lactose and tryptophan (trp) promoter systems. In addition to producing nucleic acid sequences of promoters and enhancers synthetically, sequences may be produced using recombinant cloning and/or nucleic acid amplification technology, including PCR™, in connection with the compositions disclosed herein (see U.S. Pat. Nos. 4,683,202 and 5,928,906, each incorporated herein by reference). Furthermore, it is contemplated the control sequences that direct transcription and/or expression of sequences within non-nuclear organelles such as mitochondria, chloroplasts, and the like, can be employed as well.

Naturally, it will be important to employ a promoter and/or enhancer that effectively directs the expression of the DNA segment in the organelle, cell type, tissue, organ, or organism chosen for expression. Those of skill in the art of molecular biology generally know the use of promoters, enhancers, and cell type combinations for protein expression, (see, for example Sambrook et al. 1989, incorporated herein by reference). The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or endogenous.

2. Initiation Signals and Internal Ribosome Binding Sites

A specific initiation signal also may be required for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic. The efficiency of expression may be enhanced by the inclusion of appropriate transcription enhancer elements.

3. Multiple Cloning Sites

Vectors can include a multiple cloning site (MCS), which is a nucleic acid region that contains multiple restriction enzyme sites, any of which can be used in conjunction with standard recombinant technology to digest the vector (see, for example, Carbonelli et al., 1999, Levenson et al., 1998, and Cocea, 1997, incorporated herein by reference.) "Restriction enzyme digestion" refers to catalytic cleavage of a nucleic acid molecule with an enzyme that functions only at specific locations in a nucleic acid molecule. Many of these restriction enzymes are commercially available. Use of such enzymes is widely understood by those of skill in the art. Frequently, a vector is linearized or fragmented using a restriction enzyme that cuts within the MCS to enable exogenous sequences to be ligated to the vector. "Ligation" refers to the process of forming phosphodiester bonds between two nucleic acid fragments, which may or may not be contiguous with each other. Techniques involving restriction enzymes and ligation reactions are well known to those of skill in the art of recombinant technology.

4. Splice Sites

Most transcribed eukaryotic RNA molecules will undergo RNA splicing to remove introns from the primary transcripts. Vectors containing genomic eukaryotic sequences may require donor and/or acceptor splicing sites to ensure proper processing of the transcript for protein expression (see, for example, Chandler et al., 1997, herein incorporated by reference.)

5. Termination Signals

The vectors or constructs of the present invention will generally comprise at least one termination signal. A "termination signal" or "terminator" is comprised of the DNA sequences involved in specific termination of an RNA transcript by an RNA polymerase. Thus, in certain embodiments a termination signal that ends the production of an RNA transcript is contemplated. A terminator may be necessary in vivo to achieve desirable message levels.

In eukaryotic systems, the terminator region may also comprise specific DNA sequences that permit site-specific cleavage of the new transcript so as to expose a polyadenylation site. This signals a specialized endogenous polymerase to add a stretch of about 200 A residues (polyA) to the 3' end of the transcript. RNA molecules modified with this polyA tail appear to more stable and are translated more efficiently. Thus, in other embodiments involving eukaryotes, it is preferred that that terminator comprises a signal for the cleavage of the RNA, and it is more preferred that the terminator signal promotes polyadenylation of the message. The terminator and/or polyadenylation site elements can serve to enhance message levels and to minimize read through from the cassette into other sequences.

Terminators contemplated for use in the invention include any known terminator of transcription described herein or known to one of ordinary skill in the art, including but not limited to, for example, the termination sequences of genes, such as for example the bovine growth hormone terminator or viral termination sequences, such as for example the SV40 terminator. In certain embodiments, the termination signal may be a lack of transcribable or translatable sequence, such as due to a sequence truncation.

6. Polyadenylation Signals

In expression, particularly eukaryotic expression, one will typically include a polyadenylation signal to effect proper polyadenylation of the transcript. The nature of the polyadenylation signal is not believed to be crucial to the successful practice of the invention, and any such sequence may be employed. Preferred embodiments include the SV40 polyadenylation signal or the bovine growth hormone polyadenylation signal, convenient and known to function well in various target cells. Polyadenylation may increase the stability of the transcript or may facilitate cytoplasmic transport.

7. Origins of Replication

In order to propagate a vector in a host cell, it may contain one or more origins of replication sites (often termed "ori"), which is a specific nucleic acid sequence at which replication is initiated. Alternatively an autonomously replicating sequence (ARS) can be employed if the host cell is yeast.

8. Selectable and Screenable Markers

In certain embodiments of the invention, cells containing a nucleic acid construct of the present invention may be identified in vitro or in vivo by including a marker in the expression vector. Such markers would confer an identifiable change to the cell permitting easy identification of cells containing the expression vector. Generally, a selectable marker is one that confers a property that allows for selection. A positive selectable marker is one in which the presence of the marker allows for its selection, while a negative selectable marker is one in which its presence prevents its selection. An example of a positive selectable marker is a drug resistance marker.

Usually the inclusion of a drug selection marker aids in the cloning and identification of transformants, for example, genes that confer resistance to neomycin, puromycin, hygromycin, DHFR, GPT, zeocin and histidinol are useful selectable markers. In addition to markers conferring a phenotype that allows for the discrimination of transformants based on the implementation of conditions, other types of markers including screenable markers such as fluorescent proteins, whose basis is colorimetric analysis, are also contemplated. Alternatively, screenable enzymes such as herpes simplex virus thymidine kinase (tk) or chloramphenicol acetyltransferase (CAT) may be utilized. One of skill in the art would also know how to employ immunologic markers, possibly in conjunction with FACS analysis. The marker used is not believed to be important, so long as it is capable of being expressed simultaneously with the nucleic acid encoding a gene product. Further examples of selectable and screenable markers are well known to one of skill in the art.

IV. Vector Delivery and Cell Transformation

Suitable methods for nucleic acid delivery for use with the current invention are believed to include virtually any method by which a nucleic acid (e.g., DNA) can be introduced into an organelle, a cell, a tissue or an organism, as described herein or as would be known to one of ordinary skill in the art. Such methods include, but are not limited to, direct delivery of DNA such as by ex vivo transfection (Wilson et al., 1989), by injection (U.S. Pat. Nos. 5,994,624, 5,981,274, 5,945,100, 5,780,448, 5,736,524, 5,702,932, 5,656,610, 5,589,466 and 5,580,859, each incorporated herein by reference), including microinjection (Harlan and Weintraub, 1985; U.S. Pat. No. 5,789,215, incorporated herein by reference); by electroporation (U.S. Pat. No. 5,384,253, incorporated herein by reference; Tur-Kaspa et al., 1986; Potter et al., 1984); by calcium phosphate precipitation (Graham and Van Der Eb, 1973; Chen and Okayama, 1987; Rippe et al., 1990); by using DEAE-dextran followed by polyethylene glycol (Gopal, 1985); by direct sonic loading (Fechheimer et al., 1987); by liposome mediated transfection (Nicolau and Sene, 1982; Fraley et al., 1979; Nicolau et al., 1987; Wong et al., 1980; Kaneda et al., 1989; Kato et al., 1991) and receptor-mediated transfection (Wu and Wu, 1987; Wu and Wu, 1988); by microprojectile bombardment (PCT Application Nos. WO 94/09699 and 95/06128; U.S. Pat. Nos. 5,610,042; 5,322,783 5,563,055, 5,550,318, 5,538,877 and 5,538,880, and each incorporated herein by reference); by agitation with silicon carbide fibers (U.S. Pat. Nos. 5,302,523 and 5,464,765, each incorporated herein by reference); by *Agrobacterium*-mediated transformation (U.S. Pat. Nos. 5,591,616 and 5,563,055, each incorporated herein by reference); by PEG-mediated transformation of protoplasts (U.S. Pat. Nos. 4,684,611 and 4,952,500, each incorporated herein by reference); by desiccation/inhibition-mediated DNA uptake (Potrykus et al., 1985), and any combination of such methods. Through the application of techniques such as these, organelle(s), cell(s), tissue(s) or organism(s) may be stably or transiently transformed.

V. Localization of Fusion Proteins: Fluorescence Imaging Techniques

Fluorescence imaging techniques will be used in the present invention to study the location and localization of fusion proteins targeted to GEM and non-GEM regions of cell plasma membranes. In one embodiment, confocal microscopy will be used to study the distribution of these fusion proteins on the plasma membrane surface of intact cells. In another embodiment, confocal microscopy will be used to study the distribution of fusion proteins on plamsa membranes to study the effect of a candidate substance that has been previously admixed with the cell.

Other fluorescence imaging techniques are available. By way of example, fluorescent activated cell sorting, flow cytometry, or flow microfluorometry provides the means of scanning individual cells for the presence of labeled fusion proteins. The method employs instrumentation that is capable of activating, and detecting the excitation emissions of labeled cells in a liquid medium.

FACS is unique in its ability to provide a rapid, reliable, quantitative, and multiparameter analysis on either living or fixed cells. The fusion proteins of the present invention provide a useful tool for the analysis and quantitation of GEM and non-GEM domains of individual cells. Cells would generally be obtained by biopsy, single cell suspension in blood or culture.

Flow cytometry involves the separation of cells or other particles in a liquid sample. Generally, the purpose of flow cytometry is to analyze the separated particles for one or more characteristics thereof. The basis steps of flow cytometry involve the direction of a fluid sample through an apparatus such that a liquid stream passes through a sensing region. The particles should pass one at a time by the sensor and are categorized base on size, refraction, light scattering, opacity, roughness, shape, fluorescence, etc.

Rapid quantitative analysis of cells proves useful in biomedical research and medicine. Apparati permit quantitative multiparameter analysis of cellular properties at rates of several thousand cells per second. These instruments provide the ability to differentiate among cell types. Data are often displayed in one-dimensional (histogram) or two-dimensional (contour plot, scatter plot) frequency distributions of measured variables. The partitioning of multiparameter data files involves consecutive use of the interactive one- or two-dimensional graphics programs.

Quantitative analysis of multiparameter flow cytometric data for rapid cell detection consists of two stages: cell class characterization and sample processing. In general, the process of cell class characterization partitions the cell feature into cells of interest and not of interest. Then, in sample processing, each cell is classified in one of the two categories according to the region in which it falls. Analysis of the class of cells is very important, as high detection performance may be expected only if an appropriate characteristic of the cells is obtained.

Not only is cell analysis performed by flow cytometry, but so too is sorting of cells. In U.S. Pat. No. 3,826,364, an apparatus is disclosed which physically separates particles, such as functionally different cell types. In this machine, a laser provides illumination which is focused on the stream of particles by a suitable lens or lens system so that there is highly localized scatter from the particles therein. In addition, high intensity source illumination is directed onto the stream of particles for the excitation of fluorescent particles in the stream. Certain particles in the stream may be selectively charged and then separated by deflecting them into designated receptacles. A classic form of this separation is via fluorescent tagged antibodies, which are used to mark one or more cell types for separation.

Other methods for flow cytometry can be found in U.S. Pat. Nos. 4,284,412; 4,989,977; 4,498,766; 5,478,722; 4,857,451; 4,774,189; 4,767,206; 4,714,682; 5,160,974; and 4,661,913.

In an advantageous embodiment, one may employ a second fluorescent agent that either quenches or is activated or quenched by the emission of the fluorescent fusion protein of the present invention. A particular form of this phenomenon is known as fluorescence energy transfer, or FET. FET occurs between a donor fluorophore and an acceptor dye (which may or may not be a fluorophore) when the absorption spectrum of one (the acceptor) overlaps the emission spectrum of the other (the donor) and the two dyes are in close proximity. Dyes with these properties are referred to as donor/acceptor dye pairs or energy transfer dye pairs. The excited-state energy of the donor fluorophore is transferred by a resonance dipole-induced dipole interaction to the neighboring acceptor. This results in quenching of donor fluorescence. In some cases, if the acceptor is also a fluorophore, the intensity of its fluorescence may be enhanced. The efficiency of energy transfer is highly dependent on the distance between the donor and acceptor, and equations predicting these relationships have been developed by Forster (1948). The distance between donor and acceptor dyes at which energy transfer efficiency is 50% is referred to as the Forster distance ($R_O$). Other mechanisms of fluorescence quenching are also known including, for example, charge transfer and collisional quenching.

VI. Isolation of Proteins

The present invention also provides for isolatoing and identification of proteins and polypeptides from cellular membranes. The term "purified proteins, polypeptides, or peptides" as used herein, is intended to refer to an proteinaceous composition, isolatable from mammalian cells or recombinant host cells, wherein the at least one protein, polypeptide, or peptide is purified to any degree relative to its naturally-obtainable state, i.e., relative to its purity within a cellular extract. A purified protein, polypeptide, or peptide therefore also refers to a wild-type or mutant protein, polypeptide, or peptide free from the environment in which it naturally occurs.

Generally, "purified" will refer to a specific protein, polypeptide, or peptide composition that has been subjected to fractionation to remove various other proteins, polypeptides, or peptides, and which composition substantially retains its activity, as may be assessed, for example, by the protein assays, as described herein below, or as would be known to one of ordinary skill in the art for the desired protein, polypeptide or peptide.

Various methods for quantifying the degree of purification of proteins, polypeptides, or peptides will be known to those of skill in the art in light of the present disclosure. These include, for example, determining the specific protein activity of a fraction, or assessing the number of polypeptides within a fraction by gel electrophoresis.

To purify a desired protein, polypeptide, or peptide a natural or recombinant composition comprising at least some specific proteins, polypeptides, or peptides will be subjected to fractionation to remove various other components from the composition. In addition to those techniques described in detail herein below, various other techniques suitable for use in protein purification will be well known to those of skill in the art. These include, for example, precipitation with ammonium sulfate, PEG, antibodies and the like or by heat denaturation, followed by centrifugation; chromatography steps such as ion exchange, gel filtration, reverse phase, hydroxylapatite, lectin affinity and other affinity chromatography steps; isoelectric focusing; gel electrophoresis; and combinations of such and other techniques.

Another example is the purification of a specific fusion protein using a specific binding partner. Such purification methods are routine in the art. As the present invention provides DNA sequences for the specific proteins, any fusion protein purification method can now be practiced. This is exemplified by the generation of an specific protein-glutathione S-transferase fusion protein, expression in $E.$ $coli$, and isolation to homogeneity using affinity chromatography on glutathione-agarose or the generation of a poly-histidine tag on the N- or C-terminus of the protein, and subsequent purification using Ni-affinity chromatography. However, given many DNA and proteins are known, or may be identified and amplified using the methods described herein, any purification method can now be employed.

Although preferred for use in certain embodiments, there is no general requirement that the protein, polypeptide, or peptide always be provided in their most purified state. Indeed, it is contemplated that less substantially purified protein, polypeptide or peptide, which are nonetheless enriched in the desired protein compositions, relative to the natural state, will have utility in certain embodiments.

Methods exhibiting a lower degree of relative purification may have advantages in total recovery of protein product, or in maintaining the activity of an expressed protein. Inactive products also have utility in certain embodiments, such as, e.g., in determining antigenicity via antibody generation.

VII. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Fusion Proteins Construction and Plasma Membrane Localization

Gene Construction. The separate GFP fusion proteins are outlined in FIG. 1A. Each was constructed using the GFP cloning and expression vector pWay20 (Lo et al., 1998). This vector contains a SmaI site immediately upstream of and in-frame with enhanced GFP (eGFP, Clontech, Carlsbad, Calif.) and a stop codon at the 3' end of eGFP. A CMV promoter drives gene transcription.

The GEM-targeted GFP molecule was constructed using the first 10 amino acids of $p56^{Lck}$ followed by an intermediate four-residue poly-glutamine insert, and finally eGFP itself($L_{10}$-GFP) (FIG. 1A). The polyglutamine insert was added to provide flexibility between the adjacent protein domains (Minor and Kim, 1994). The oligonucleotides used for encoding the N-terminal region of $p56^{Lck}$ and the poly-glutamine spacer were: ATGGGCTGTGTCTGCAGCT-CAAACCCTGAAAACAACAACAAC (coding; SEQ ID NO:1) and GTTGTTGTTGTTTTCAGGGTTTGAGCTG-CAGACACAGCCCAT (noncoding SEQ ID NO:2). For construction of the gene, the oligonucleotides were annealed and subcloned into SmaI-cut pWay20.

The GFP-labeled marker for the non-GEM compartment consists of the first 15 amino acids of $pp60^{c-Src}$ followed by a poly-glutamine spacer and eGFP ($S_{15}$-GFP) (FIG. 1A). The oligonucleotides encoding the membrane-anchoring domain and poly-glutamine insert were: ATGGGGAGCAG-CAAGAGCAAGCCCAAGGACCCCAGC-CAGCGCCGGAACAACAACAA (coding; SEQ ID NO:3) and GTTGTTGTTGTTCCGGCGCTG-GCTGGGGTCCTTGGGCTTGCTCTTGCTGCTCCCCAT (noncoding; SEQ ID NO:4).

Cell Lysis and Equilibrium Centrifugation. Cells were lysed with 1% Triton X-100 (TX-100) and the samples prepared as described previously (Rodgers and Rose, 1996). The GEM and TX-100-soluble (TXS) membrane fractions were separated by equilibrium centrifugation using a discontinuous sucrose gradient. The gradient consisted of 1.75 ml of a 30% sucrose solution overlaid with 0.75 ml of a 5% sucrose solution. Centrifugation was performed using a SW rotor. All sucrose solutions were in 10 mM Tris-HCl (pH 7.5), 150 mM NaCl, and 5 mM EDTA (TNE). The samples were centrifuged for 16–18 hr at 200000×g. Following centrifugation, the gradients were harvested by fractionating from the top. Each gradient fraction was separated by SDS-PAGE, and $L_{10}$- and $S_{15}$-GFP were detected by immunoblotting using monoclonal antibody specific to GFP (Covance Research Products, Inc., Richmond, Calif.).

Cell Stimulation. Polystyrene beads coated with OKT3 monoclonal antibody specific to CD3 were prepared as described (Lowin-Kropf et al., 1998) Cells were stimulated by incubating $10^6$ cells with $5 \times 10^5$ beads for 15 min at 30° C. Following incubation, the cell-bead mixture was seeded onto poly-L-lysine coated coverslips by incubating at room temperature for 5 min. The cells were fixed using 2% paraformaldehyde for 30 min at room temperature. To measure capping of F-actin, the cells were labeled with Texas Red-conjugated phalloidin as described (Rodgers and Zavzavadjian, 2001).

Measurement of Association with GEM Domains. To measure association of either $L_{10}$- or $S_{15}$-GFP with GEM domains, membrane fractionation experiments were performed using Jurkat cells expressing either construct. In this experiment, the GEM and non-GEM compartments were separated by sucrose gradient equilibrium centrifugation. For this, the cells are first lysed with TX-100, during which the GEM domains form membrane sheets and vesicles. The GEM fraction in the cell lysate is then separated from the detergent-soluble non-GEM fraction by equilibrium centrifugation (Brown and Rose, 1992). FIG. 1B shows that $L_{10}$-GFP is present in the GEM fraction represented by gradient fractions 1 through 4. Conversely, $S_{15}$-GFP occurs only in the TX-100-soluble fraction of the membrane represented by gradient fractions 6 through 10. Quantitation showed that approximately 55% of the total $L_{10}$-GFP is present in the GEM fraction, and this is similar to that of wild-type $p56^{Lck}$ in Jurkat cells (Rodgers and Rose, 1996). Altogether, FIG. 1B shows that the GEM- and non-GEM targeting signals efficiently target GFP to the respective membrane compartments as measured by sucrose gradient equilibrium centrifugation of TX-100 lysates.

Figure 2A:
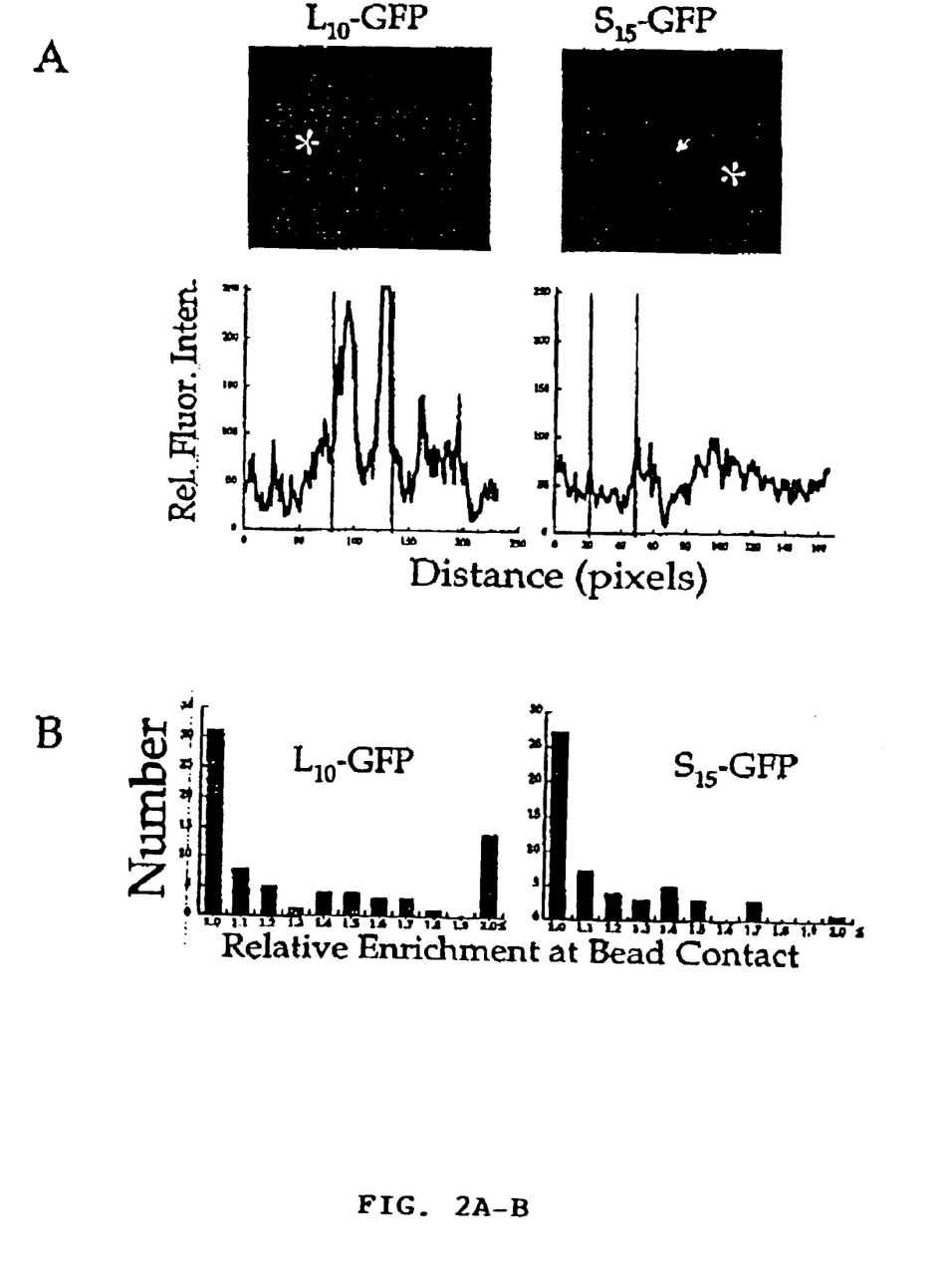
(FIG. 2A) Jurkat cells expressing L$_{10}$-GFP (left) or S$_{15}$-GFP (right) were stimulated using polystyrene beads coated with antibody specific to CD3. The asterisk indicates the position of the beads. The plots in FIG. 2A represent quantitation of the fluorescence intensity of the plasma membrane of each image. The y-axis of each plot represents the relative fluorescence intensity of the plasma membrane, and it has arbitrary units ranging in value between 0 and 255. The x-axis represents the distance around the perimeter of the cell, and each pixel represents 0.25 μm. The region of the graph corresponding to the bead-contact site in the plasma membrane is marked by the red lines.

Jurkat cells expressing either $L_{10}$- or $S_{15}$-GFP are shown in FIG. 2A. Importantly, the images show that $L_{10}$- and $S_{15}$-GFP are membrane associated, with the majority of the signal occurring in the plasma membrane. In many cells, $L_{10}$-GFP and $S_{15}$-GFP were also enriched in intracellular structures that probably represent early endosomes (Ley et al., 1994). An example of this is indicated by the arrow in the image of the cell expressing $S_{15}$-GFP.

Example 2
T Cell Stimulation and Targeting of GEM Domains by Fusion Proteins

Stimulation of T cells by antibody-mediated crosslinking of the T cell receptor (TcR) results in patching of GEM domains at the site of TcR crosslinking (Janes et al., 1999). Importantly, FIGS. 2A-B shows $L_{10}$-GFP is selectively enriched in membrane caps that form as a result of crosslinking of the TcR by OKT3-coated bead. For example, each cell shown in FIG. 2A has bound an OKT3-coated bead, and the asterisk indicates this. In the cell expressing $L_{10}$-GFP, the fluorescence is enriched in the region of the plasma membrane contacting the bead. Conversely, $S_{15}$-GFP is not enriched in a membrane cap. Actin staining using phalloidin confirmed that a membrane cap was present at the bead contact site in the $S_{15}$-GFP sample (data not shown). Furthermore, the amount of enrichment of the respective GFP constructs at the bead contact site was quantitated by measuring the fluorescence intensity of the plasma membrane around the perimeter of the cell. The fluorescence intensity profile for each experiment is shown in the bottom panels in FIG. 2A. The red lines indicate the region of the plasma membrane that contacts the antibody-coated bead. These results show there is approximately a 5-fold enrichment of $L_{10}$-GFP at the bead contact site, but no significant enrichment of $S_{15}$-GFP. Thus, $L_{10}$-GFP is selectively targeted to GEM domains that occur in TcR caps in stimulated T cells.

Targeting of either $L_{10}$-GFP or $S_{15}$-GFP to membrane caps was measured in populations of cells stimulated with OKT3-coated beads. Histograms showing the distribution of protein enrichment values in membrane caps are shown in FIG. 2B. In the $L_{10}$-GFP sample, approximately one-third of the cells exhibited a 2.0-fold or greater enrichment of the GFP in the membrane caps. Conversely, essentially none of the cells expressing $S_{15}$-GFP exhibited significant enrichment of fluorescence in membrane caps. Thus, the histograms in FIG. 2B correlated with FIG. 2A showing selective targeting of GFP to membrane caps by the $L_{10}$ sequence. Based on the data in FIGS. 1A-B and FIGS. 2A-B, it is concluded that $L_{10}$-GFP is efficiently targeted to GEM domains, and that $S_{15}$-GFP is excluded from this membrane compartment.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 3,826,364
U.S. Pat. No. 4,284,412
U.S. Pat. No. 4,498,766
U.S. Pat. No. 4,659,774
U.S. Pat. No. 4,661,913
U.S. Pat. No. 4,680,338
U.S. Pat. No. 4,682,195
U.S. Pat. No. 4,683,202
U.S. Pat. No. 4,684,611
U.S. Pat. No. 4,714,682
U.S. Pat. No. 4,767,206
U.S. Pat. No. 4,774,189
U.S. Pat. No. 4,816,571
U.S. Pat. No. 4,857,451
U.S. Pat. No. 4,952,500
U.S. Pat. No. 4,959,463
U.S. Pat. No. 4,989,977
U.S. Pat. No. 5,141,648
U.S. Pat. No. 5,141,813
U.S. Pat. No. 5,160,974
U.S. Pat. No. 5,264,566
U.S. Pat. No. 5,302,523
U.S. Pat. No. 5,322,783
U.S. Pat. No. 5,384,253
U.S. Pat. No. 5,428,148
U.S. Pat. No. 5,464,765
U.S. Pat. No. 5,478,722
U.S. Pat. No. 5,538,877
U.S. Pat. No. 5,538,880
U.S. Pat. No. 5,550,318
U.S. Pat. No. 5,554,744
U.S. Pat. No. 5,563,055
U.S. Pat. No. 5,563,250
U.S. Pat. No. 5,574,146
U.S. Pat. No. 5,580,859
U.S. Pat. No. 5,589,466
U.S. Pat. No. 5,591,616
U.S. Pat. No. 5,602,244
U.S. Pat. No. 5,610,042
U.S. Pat. No. 5,645,897
U.S. Pat. No. 5,656,610
U.S. Pat. No. 5,702,932
U.S. Pat. No. 5,736,524
U.S. Pat. No. 5,780,448
U.S. Pat. No. 5,789,215
U.S. Pat. No. 5,856,456
U.S. Pat. No. 5,880,270
U.S. Pat. No. 5,928,906
U.S. Pat. No. 5,945,100
U.S. Pat. No. 5,981,274
U.S. Pat. No. 5,994,624
U.S. Pat. No. 6,172,188

Ausubel, Brent, Kingston, Moore, Seidman, Smith, Struhl, In: *Current Protocols in Molecular Biology*, John, Wiley & Sons, Inc, New York, 1994.
Brown and Rose, *Cell*, 68:533–544, 1992.
Carbonelli, Corley, Seigelchifer, Zorzopulos, *FEMS Microbiol Lett*, 177(1):75–82, 1999.
Chandler, Mayeda, Yeakley, Krainer, Fu, *Proc Natl Acad Sci USA*, 94(8):3596–601, 1997.
Chen and Okayama, *Mol. Cell Biol.*, 7(8):2745–2752, 1987.
Cocea, *Biotechniques*, 23(5):814–816, 1997.
EP 266 032
Fechheimer, Boylan, Parker, Sisken, Patel, Zimmer, *Proc. Nat'l Acad. Sci. USA*, 84:8463–8467, 1987.
Forster, 1948. *Ann. Phys.* 2, 55–75, 1948.
Fraley et al., *Proc. Nat'l Acad. Sci. USA*, 76:3348–3352, 1979.
Gopal, *Mol. Cell Biol.*, 5:1188–1190, 1985.
Graham and van der Eb, *Virology*, 52:456–467, 1973.
Harland and Weintraub, *J. Cell Biol.*, 101:1094–1099, 1985.
Heim and Tsien, "Engineering green fluorescent protein for improved brightness, longer wavelengths and fluorescence resonance energy transfer" *Current Biology* 1996, 6:178–182.
Janes, Ley, Magee, *J. Cell Biol.*, 147:447–61, 1999.
Kabouridis, Magee, Ley, *Embo. J.*, 16:4983–98, 1997.
Kaneda et al., *Science*, 243:375–378, 1989.
Karnitz, Sutor, Torigoe, Reed, Bell, McKean, Leibson, Abraham, *Mol. Cell Biol.*, 12:4521–30, 1992.
Kato et al., *J. Biol. Chem.*, 266:3361–3364, 1991.
Kwong and Lublin, *Biochem. Biophys. Res. Commun.*, 207:868–76, 1995.
Levenson, Transue, Roninson, *Hum Gene Ther*, 9(8):1233–6, 1998.
Ley, Marsh, Bebbington, Proudfoot, Jordan, *J. Cell Biol.*, 125:639–49, 1994.
Lo, Rodgers, Hughes, *Biotechniques*, 25:94–96, 1998.
Lowin-Kropf, Shapiro, Weiss, *J. Cell Biol.*, 140:861–71, 1998.
Minor and Kim, *Nature*, 367:660–3, 1994.
Miyawaki, Llopis, Heim, McCaffery, Adams, Ikura, and Tsien, "Fluorescent indicators for Ca2+based on green fluorescent proteins and calmodulin" *Nature* vol. 388, pp. 882–887, 1997
Nicolau and Sene, *Biochim. Biophys. Acta*, 721:185–190, 1982.
Nicolau et al., *Methods Enzymol.*, 149:157–176, 1987.
Potrykus, Paszkowski, Saul, Petruska, Shillito, *Mol Gen Gene.t*, 199(2):169–77, 1985.
Potter et. al., *Proc. Nat'l Acad. Sci. USA*, 81:7161–7165, 1984.
Resh, *Cell* 76:411–3, 1994.
Rippe, Brenner and Leffert, *Mol. Cell Biol.*, 10:689–695, 1990.
Rodgers and Rose, *J. Cell Biol.*, 135:1515–23, 1996.
Rodgers, Crise, Rosek, *Mol. Cell Biol.*, 14:5384–91, 1994.
Sambrook et al., "Molecular Cloning," *A Laboratory Manual*, 2d Ed., Cold Spring Harbor Laboratory Press, New York, 13.7–13.9:1989.
Shenoy-Scaria, Dietzen, Kwong, Link, Lublin, *J. Cell Biol.*, 126:353–63, 1994.
Shenoy-Scaria, Gauen, Kwong, Shaw, Lublin, *Mol. Cell Biol.*, 13:6385–92, 1993.
Simons and Toomre, *Nature Mol. Cell Biol. Rev.* 1:31–39, 2000.
Straus and Weiss, *Cell*, 70:585–93, 1992.
Tur-Kaspa, Teicher, Levine, Skoultchi and Shafritz, *Mol. Cell Biol.*, 6:716–718, 1986.
Wawrzynczak & Thorpe, 1987
Wilson et al., *Science*, 244:1344–1346, 1989.
WO 94/09699
WO 95/06128
WO 95/07463
Wong et al., *Gene*, 10:87–94, 1980.
Wu and Wu, *J. Biol. Chem.*, 262:4429–4432, 1987.
Wu and Wu, *Biochemistry*, 27:887–892, 1988.
Xavier, Brennan, Li, McCormack, Seed, *Immunity*, 8:723–32, 1998.
Yurchak and Sefton, *Mol. Cell Biol.*, 15:6914–22, 1995.

What is claimed is:

1. A polynucleotide that encodes a fusion protein comprising:
   (a) a peptide of 5 to about 15 consecutive amino acid residues comprising a membrane targeting sequence from $p56^{Lck}$;
   (b) a fluorescent protein; and
   (c) a linker inserted between, and covalently bound to, said membrane targeting sequence and said fluorescent protein.

2. The polynucleotide of claim 1, wherein said targeting sequence is 5, 6, 7, 8, 9, 10, 11, 12, 13, 14, or 15 amino acid residues in length.

3. The polynucleotide of claim 1, wherein said targeting sequence is the first 10 amino acid residues of $p56^{Lck}$.

4. The polynucleotide of claim 1, wherein said targeting sequence and said linker are encoded by the oligonucleotide ATGGGCTGTGTCTGCAGCTCAAACCCT-GAAAACAACAACAAC (SEQ ID NO:1).

5. The polynucleotide of claim 1, wherein said linker is a poly-glutamine peptide of about 4 amino acid residues in length.

6. The polynucleotide of claim 1, wherein the fluorescent protein is green fluorescent protein, yellow fluorescent protein or cyan fluorescent protein.

7. An expression vector comprising a polynucleotide comprising:
   (a) a fusion protein coding region comprising:
      (i) a peptide of 5 to about 15 consecutive amino acid residues comprising a membrane targeting sequence from $p56^{Lck}$;
      (ii) a fluorescent protein;
      (iii) a linker inserted between, and covalently bound to, said membrane targeting sequence of said fluorescent protein; and
   (b) a promoter operatively linked to said fusion protein coding region.

8. The expression vector of claim 7, wherein said expression vector is pWay20.

9. The expression vector of claim 7, wherein said promoter is a CMV promoter.

10. The expression vector of claim 7, wherein the fluorescent protein is green fluorescent protein, yellow fluorescent protein or cyan fluorescent protein.

* * * * *